United States Patent [19]

Price

[11] 4,264,559
[45] Apr. 28, 1981

[54] MIXING DEVICE FOR MEDICAL LABORATORY TESTS

[76] Inventor: William F. Price, 705 S. Fourth St., Folkston, Ga. 31537

[21] Appl. No.: 73,213

[22] Filed: Sep. 7, 1979

[51] Int. Cl.³ .................... B01F 11/00; G01N 33/48
[52] U.S. Cl. ................................. 422/99; 422/102; 422/104; 366/112
[58] Field of Search ............... 366/108, 110, 111, 112, 366/113, 114; 422/99, 102, 104

[56] References Cited

U.S. PATENT DOCUMENTS 4,102,649  7/1978  Sasaki ................................. 422/99

Primary Examiner—Michael S. Marcus

[57] ABSTRACT

A device which can be used in certain chemical and medical laboratory tests wherein very small quantities of fluids (such as micro-liters) are used (as in such as the Rubacell test for immunity to Rubella). In performing such tests the small quantities are contained in a container called a "V" plate, or like container, which container has small wells to contain the fluids and small upward depressions on its bottom aspect.

1 Claim, 3 Drawing Figures

MIXING DEVICE FOR MEDICAL LABORATORY TESTS

This present invention relates to a device which can be used in certain chemical and laboratory tests wherein very small quantities of fluids (such as micro-liters) are used and these very small quantities are measured into small containing holes of multiple container devices or like and need agitation or a method of positive disperse-ment one fluid and/or emulsification with another.

In such tests in which minute quantities of liquid of small matter are dispersed in liquids they must be properly mixed in order to give proper repeatable results. Presently the suppliers of such reagents used in such tests give varying instructions to users, the supplier of the "V" plate (Abbott Laboratories) give instructions to users to;

"Tap "V" plate as follows to ensure that specimen dilution Buffer spreads over the bottom of each well. Hold "V" plate at an angle of approximately 45 degrees to the work surface and tap lower edge firmly on work surface, repeat for each plate edge" which tapping must be repeated upon addition of specimen serums and control serums, then after addition of sensitized cells (all noted for the test for immunity to Rubella).

Using this new invention the container or multiple container holder device into which ingredients have been placed and are mixed together to react is placed upon this mixer so that one of the upward depressions in its bottom (the bottom of the multiple container) or whatever holder contains the fluid to be mixed fitting over an upward rising prong 18 upon a length of a spring-like metal length 1A, one end of which is tightly unmoveably fixed on an upright mounting means 3 fixed tightly unmoveably at one end of the mixed base 9 and the multiple container or other holder overlaps the second or more springlike metal lengths 1B for further support and balance upon the mixer and the free ends of one or the other of springlike lengths 1A or 1B which are coupled at their free swingling ends by coupling means 16 is plucked (as a banjo string) so that both springlike metal lengths 1A and 1B bound together at the coupled moveable ends repeatedly vibrate back-and-forth oscillatingly for a short period of time, that amount of rapid vibrational movement controllable and variable because of the movable location of the clamped prong 16 upon springlike metal length 1A (or 1B) in a manner to properly mix the contents of whatever container has been placed upon the device.

With this invention no electrical energy or involved tapping is involved, only a plucking by the finger of the operator. The very limited back-and-forth movement of the container or tray causes greatest possible turbulence while its confined movements are so short they cause no sloshing of the contents of the containers.

With the above and other objects in view as will be apparent, this invention consists in the construction, combination, and arrangement of parts all as herein more fully described, claimed, and illustrated by the accompanying drawings wherein;

DETAILED DESCRIPTION OF DRAWINGS

Figure 1:
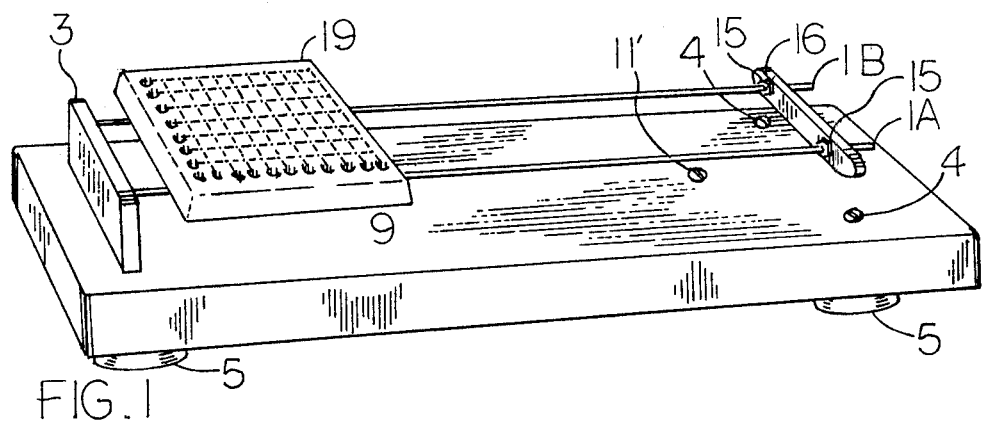
FIG. 1. A perspective drawing of the mixer revealing the base 9 with its upright mount 3 into which springlike metal lengths 1A and 1B are force mounted into holes 2 (seen FIG. 3), upright clamped prong 18 clamped upon one such springlike metal length 1A (or 1B) in such a way it is movable upon loosening which movement causes it more or less lateral motion in use, and coupling mass 16 at the freely movable ends of springlike metal lengths 1A and 1B, weight of coupling device 16 accounting by its mass for distance and speed of vibrational movement of springlike metal lengths 1A and 1B, and duration of that movement, which movement is imparted to clamped prong 18 and consequentally to mixing container 19 which was placed with its upward-built-in depression fitting over clamped prong 18 before springlike metal lengths 1A or 1B were plucked. Cushion feet 5 are seen at front bottom of base 9 but invisible this Figure at back side of base 9.

FIG. 1 is a perspective of mixer revealing base 9 with its upright fixed mount 3 into which springlike metal lengths 1A and 1B are mounted, upright clamped prong 18 clamped upon one length of such springlike metal length 1A in such a manner it is moveable closer or further from the upright mount 3 along that springlike metal length 1A making it adjustable to move the specimen holding means or tray 19 in a shorter or more distant vibrational movement when end of springlike metal length 1A or 1B is plucked, and coupling mass 16 of weight at movable end of springlike metal lengths 1A and 1B, weight of its mass accounting for distance of movement and rapidity of vibration imparted to the specimen container placed upon clamped prong 18 by the pendulumlike vibrations of springlike metal lengths 1A and 1B whenever movable ends of springlike metal lengths 1A or 1B are plucked at the freely movable ends connected by coupling 16. Cushion feet 5 can be seen on bottom front corners of base 9 as well as mounting bolt 4' but mounting bolts 4 enter base 9 from below and cannot be seen nor can cushion feet 5 be seen on bottom backside of base 9.

Figure 2:
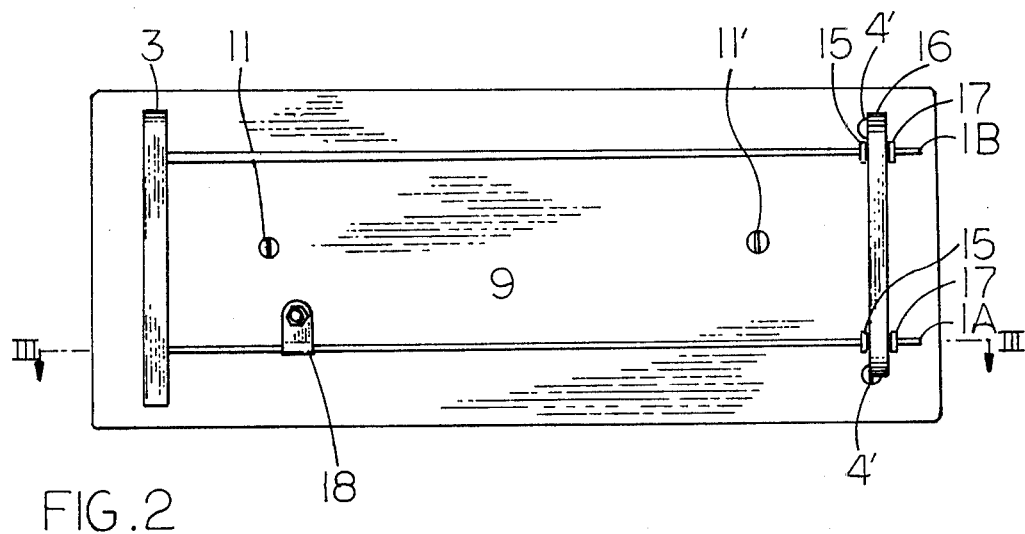
FIG. 2. Vertical view upon parts visible with placement of parts including bolts 11 and 11' and bolts 4' which attach the ballast weights 7 and 7' to base 9 if hollow base 9 is used. Bolts 4' also are fixing attachment of cushion feet 5 to bottom of base 9.

FIG. 2 is a view from above looking vertically upon the invention showing parts visible therefrom, base 9, upright supporting mounting means 3, the support mechanism or cantilevered support arms (springlike metal lengths) 1A and 1B which support the container for samples mounted in holes 2 (seen in FIG. 3) and clamped prong 18 which imparts movement of vibrational springlike metal lengths 1A and 1B to the specimen holder (container for samples) 19 or other holding means for specimens. Coupling means 16 for freely movable ends of springlike metal lengths 1A and 1B is shown anchored in place by anchoring nuts 15 and 17. Heads of screws or bolts 11 and 11' are shown which bolts are part of the assembly holdings for ballast weights 7 and 7' not visible in this view, part of base 9.

Figure 3:
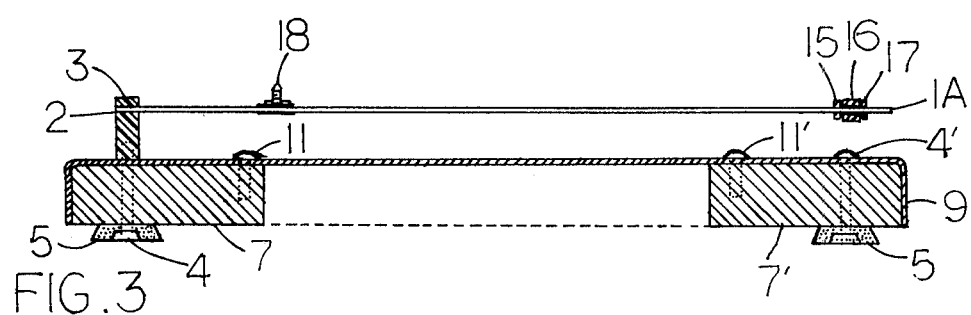
FIG. 3. Cross section along the line III of FIG. 2 showing base 9 to which upright mounting means 3 is affixed and springlike metal lengths 1A and 1B embedded in holes 2 of mount 3 and extending toward their free swinging ends which are coupled together by coupling means 16 retained in position by nuts 15 and 17 on threaded ends of springlike metal lengths 1A and 1B illustrating sample holder connecting clamped prong 18 clamped in position on springlike metal length 1A. Suchion foot 5 at the mounting means 3 end of the base 9 is attached to base 9 by screw or bolt 4 which passes upward through a washer means then the cushion foot, then through ballast weight 7, then base 9 and is screwed or bolted into tapped holes in upright mounting means 3 to affix the multiplicity of parts.

FIG. 3 is a cross sectional view along the line III of FIG. 2. The base 9 in this case consists of sheet metal or perhaps plastic bent or moulded flat upside down tray with heavy material ballast 7 and 7' to assure it stability and anchoring upon the surface upon which it must operate, upright mounting means 3 coupled to base 9 at one end by bolts 4 from below (these and other features shown in dotted lines since they are not in plane of line III of FIG. 2) and the two springlike metal lengths 1A and 1B coupled to the upright mounting means 3 which springlike metal lengths 1A and 1B extend outwardly toward opposite ends of said base 9, and coupling means 16 and metal lengths 1A and 1B supported in cantilevered manner, upright clamped prong 18 which clamped prong 18 may be moved to change positions of said clamped prong 18 changing the amount of lateral vibrational movement imparted to samples being tested by shaking with pendulumlike vibrational motions of the springlike metal lengths 1A and 1B coupled by coupling mass 16 when plucked.

IT IS TO BE UNDERSTOOD that I have shown and described herein my present invention in its form and embodiment. Other and further modifications may suggest themselves to persons skilled in the art and all such modifications to the extent they embody the principles of the invention as pointed out in the appended claim are to be considered within the scope and purview thereof.

Having thus described my present invention what I now claim and desire to secure by Letters Patent is:

1. A mixing device for liquid samples comprising means defining a horizontal base, upright mounting means connected to an upper surface of said base means and located at one end thereof, horizontally disposed springlike metal lengths connected at one end to an upright mounting means and extending outwardly toward the opposite end of said base means and terminating in free ends; said metal lengths being supported in cantilevered manner, coupling means connected to said free ends of said metal lengths to maintain the same in spaced configuration, mixing container means for holding a plurality of samples and an adjustable attachment means mounted on one such metal length for attachment to said container means whereby samples in said container means are mixed when said container means is attached to said attachment means and said free ends of said metal lengths are plucked.

* * * * *